Figure 1:
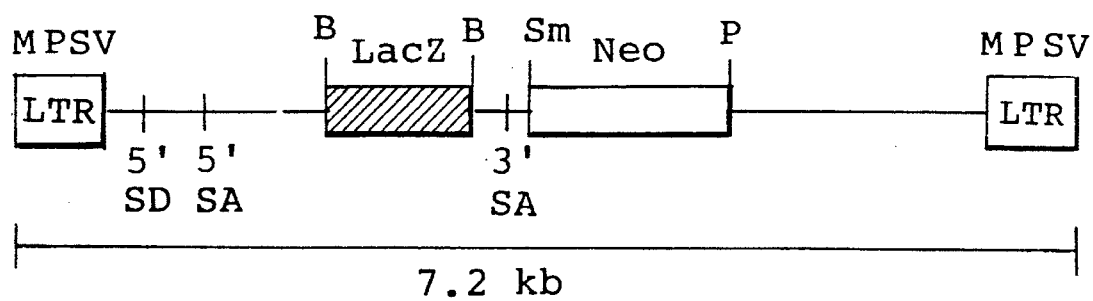

United States Patent [19]

Gerson et al.

[11] Patent Number: 5,591,625
[45] Date of Patent: Jan. 7, 1997

[54] TRANSDUCED MESENCHYMAL STEM CELLS

[75] Inventors: Stanton L. Gerson, Pepper Pike; Arnold I. Caplan; Stephen E. Haynesworth, both of Cleveland Heights, all of Ohio

[73] Assignee: Case Western Reserve University, Cleveland, Ohio

[21] Appl. No.: 158,000

[22] Filed: Nov. 24, 1993

[51] Int. Cl.$^6$ .............................. C12N 5/10; C12N 5/08; C12N 15/86; A61K 48/00

[52] U.S. Cl. .................. 435/240.2; 424/93.7; 424/93.21; 435/172.3; 435/320.1; 935/62; 935/70; 935/71

[58] Field of Search ............................ 435/240.2, 172.3, 435/320.1; 424/93.7, 93.21; 935/62, 70, 71

[56] References Cited

U.S. PATENT DOCUMENTS

| | | | |
|---|---|---|---|
| 3,968,567 | 7/1976 | Nevins | 433/224 |
| 4,254,226 | 3/1981 | Eisinger et al. | 435/240.23 |
| 4,430,760 | 2/1984 | Smestad | 623/10 |
| 4,596,574 | 6/1986 | Urist | 623/16 |
| 4,609,551 | 9/1986 | Caplan et al. | 424/549 |
| 4,642,120 | 2/1987 | Nevo et al. | 623/16 |
| 4,714,680 | 12/1987 | Civin | 435/240.25 |
| 4,721,096 | 1/1988 | Naughton et al. | 128/898 |
| 4,904,259 | 2/1990 | Stay | 623/16 |
| 5,197,985 | 3/1993 | Caplan et al. | 623/16 |
| 5,206,023 | 4/1993 | Hunziker | 424/423 |
| 5,226,914 | 7/1993 | Caplan et al. | 623/16 |
| 5,399,346 | 3/1995 | Anderson et al. | 424/93.21 |
| 5,486,359 | 1/1996 | Caplan et al. | 424/93.7 |

FOREIGN PATENT DOCUMENTS

| | | |
|---|---|---|
| 0243204 | 10/1987 | European Pat. Off. . |
| WO87/00201 | 1/1987 | WIPO . |
| WO88/08306 | 11/1988 | WIPO . |
| WO89/02468 | 3/1989 | WIPO . |
| WO89/05345 | 6/1989 | WIPO . |
| WO89/07136 | 8/1989 | WIPO . |
| WO90/10872 | 3/1990 | WIPO . |
| WO90/02806 | 3/1990 | WIPO . |
| WO90/11359 | 10/1990 | WIPO . |
| WO92/07573 | 5/1992 | WIPO . |
| WO92/07943 | 5/1992 | WIPO . |
| WO92/12242 | 7/1992 | WIPO . |

OTHER PUBLICATIONS

F. D. Ledley (1991) Human Gene Therapy 2:77–83.
A. I. Caplan (1991) Journal of Orthopaedic Research 9(5):641–650.
S. P. Bruder et al. (1994) Journal of Cellular Biochemistry 56:283–294.
J. Allay et al. (1993) Blood 82(10), Suppl. 1:477a, Abstract 1893.
H. Chemes et al. (1992) Biology of Reproduction 46:793–801.
B. M. Thomson et al. (1993) Bone 14:779–786.
Haynesworth et al, Bone, vol. 13(1) (1992) pp. 81–88.
Miller, Nature, vol. 357, 11 Jun. 1992 pp. 455–460.
Yoneda et al., Science, vol. 213 (31 Jul. 1981) pp. 563–565.
Markowitz, Virology, 167 (1988) pp. 400–406.
Haynesworth et al, Bone, vol. 13(1) (1992) pp. 69–80 .
Clapp et al., Blood, vol. 78 (1991) pp. 1132–1139.
Gilboa, BioEssay, vol. 5 (1986) pp. 252–257.
Hock et al, Nature vol. 320 (20 Mar. 1986) pp. 275–277.
Franzen et al., *Differentiation*, 36:199–210 (1987).
Goshima et al., *Clin. Orthop. & Rel. Res.*, 269:274–283 (1991).
Goshima et al., *Clin. Orthop.* 262:298–311 (1991).
Nakahara et al., *J. Orthop. Res.*, 9:465–476.
Linsenmeyer et al., *Biochem. Biophys. Res. Comm.*, 92 (2): 440–446 (1980).
Ashton et al., *Calcif. Tissue Int.*, 36:83–86 (1984).
Bruder et al., *Bone and Mineral*, 11:141–151 (1990).
Goding et al., *Monoclonal Antibodies: Principles and Practice*, Academic Press (NY), pp. 56–97 (1983).
Freshney, "Culture of Animal Cells", Alan R. Liss, NY, pp. 162–165 and 187–190 (1987).
Grigoriadis et al., *J. Cell. Biol.*, 106:2139–2151 (1988).
Kipps et al., in Weir (Ed.), *Handbook of Expt'l Immunol*, Blackwell Scientific Publ. (London), vol. 4, pp. 108.1–108.9 (1986).
Harlow et al., *Antibodies: a Laboratory Manual* (vol. 4), Cold Spring Harbour, pp. 153–154, 392–393 and 578–581 (1988).
Kasid, et al., Proc. Natl. Acad. Sci. USA, 87:473–477 (1990).
Thompson, Time Magazine, Jun. 7, 1993, pp. 50–53.
ATCC Catalog, 7th Ed., 1992, p. 144.
GIBCO BRL Catalog, 1990, pp. 1, 12, 15, 16, 55, 199, 202–203.
Buderi, *The Scientist*, Jan. 23, 1989, pp. 1–3.
Siegel, *Los Angeles Times*, Dec. 13, 1987, pp. 1, 37–40.
Williams, *Nature*, 310:476–480 (1984).
Dick et al., *Cell*, 42:71–79 (1985).
Keller et al., *Nature*, 318:149–154 (1985).
Rosenberg et al., *Science*, 233:1318–1321 (1986).
Kantoff et al., *Genetics*, 83:6563–6567 (1986).
Armentano et al., *J. Virol.*, 61:1647–1650 (1987).

(List continued on next page.)

*Primary Examiner*—Mindy Fleisher
*Assistant Examiner*—Johnny F. Railey, II
*Attorney, Agent, or Firm*—Charles J. Herron; Elliot M. Olstein

[57] ABSTRACT

Genetically engineered human stem cells that carry within them genes of interest particularly for the expression of physiologically or pharmacologically active proteins or for use in gene therapy. In addition to correction of genetic disorders, is the ability to introduce, in a targeted manner, additional copies of essential genes to allow expression in proliferating, nondifferentiating cells of certain gene products. These genes can be, for example, hormones matrix proteins, cytokines, adhesion molecules, detoxification enzymes and "rebuilding" proteins important in tissue repair.

21 Claims, 7 Drawing Sheets

OTHER PUBLICATIONS

Armentano et al., *Journal of Virology*, 61:1647–1650 (1987).
Selden et al., *Science*, 236:714–718 (1987).
Siegel, *Los Angeles Times*, 1, 37–38, 40 (Dec. 13, 1987).
Siegel, *Los Angeles Times*, 22–24 (Dec. 14, 1987).
Culver et al., *J. Cellular Biochem., Suppl.* 12B:171 (1988).
Williams et al., *Blood*, 71:1738–1743 (1988).
Rosenberg et al., *New England Journal of Med.*, 319:1676–1680 (1988).
Ruderi, *The Scientist*, 3(2):1–2 (1989).
Wilson, *Science*, 244:1344–1346 (1989).
Dumenco, *Cancer Research*, 49:6044–6051 (1989).
Anderson, *Human Gene Therapy*, 1:331–362 (1990).
Morgan et al., *Aids Research & Human Retroviruses*, 6:183–191 (1990).
Wilson, *Proc. Natl. Acad. Sci.*, 87:439–443 (1990).
Kaleko, *Blood*, 75:1733–1741 (1990).
Rosenberg, *New Eng. Journal of Med.*, 323(9):570–578 (1990).
Rosenberg, *Journal of Nat'l Cancer Institute*, 82:1380–1381 (1990).
Jaroff, *Time*, 74–76 (Sep. 24, 1990).
Anderson et al., *recombinant DNA Technical Bulletin*, 13:245–272 (1990).
Clopp et al., *Am. Society of Hematology*, 1132–1139 (1991).
Wieder et al., *Blood*, 77(3):448–455 (1991).
Beck–Engeser et al., *Human Gene Therapy*, 2:61–70 (1991).
Ledley, *Human Gene Therapy*, 2:77–83 (1991).
Schuening, *Blood*, 78:2568–2576 (1991).
Miller, *Nature*, 357:455–460 (1992).
Luskey et al., *Blood*, 80(2):396–402 (1992).
Eagington, *BioTechnology*, 10:1099–1106 (1992).
Thompson, *Time*, 50–53 (Jun. 7, 1993).
Challita et al., *Proc. Nat'l Acad. Sci.*, 91:2567–2571 (1994).
Krall et al., *Blood*, 83(9):2737–2748 (1994).
Riviere et al., *Proc. Nat'l Acad. Sci.*, 92:6733–6737 (1995).

F I G. 4
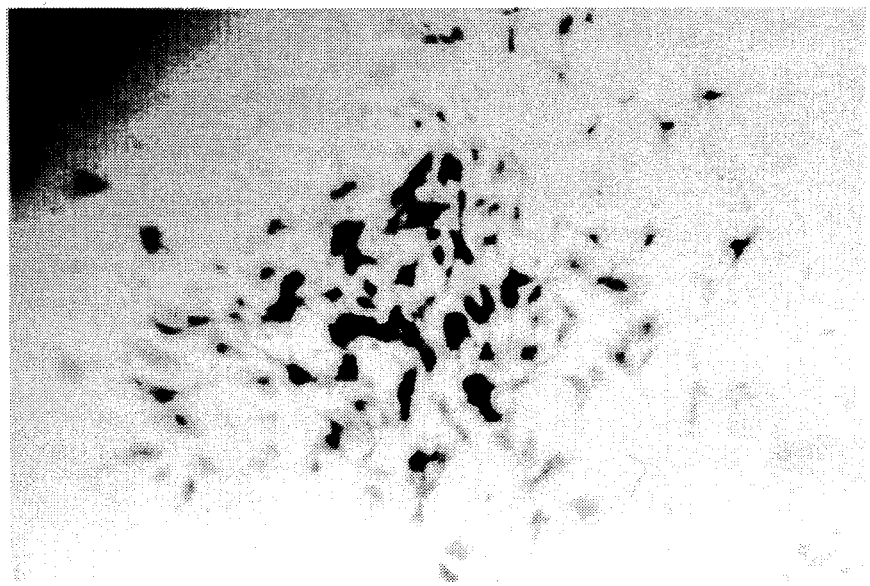

TRANSDUCED MESENCHYMAL STEM CELLS

The present invention is directed to a totally unexplored application of human stem cells, i.e. that of genetically engineered cell that carry within them genes of interest particularly for the expression of physiologically or pharmacologically active proteins or for use in gene therapy.

In accordance with the present invention it has been discovered that human mesenchymal stem cells (MSCs) or human mesenchymal progenitor cells can be used as host cells for the expression of exogenous gene products. One aspect of the invention relates to the discovery and development of the technology to isolate these cells, mitotically proliferate them in cell culture and introduce them back in vivo into the same recipient. These culture-expanded cells home back to the marrow and enhance hematopoietic recovery in the marrow transplant setting. Furthermore, these cells can be manipulated for cellular therapy, e.g. expanded, purified, selected and maintained for clinical use while still mantaining their precursor phenotype. Part of this manipulation is the characterization of such cells and their cryopreservation for future use.

Mesenchymal stem cells (MSCs) can be derived from marrow, periosteum, dermis and other tissues of mesodermal origin. They are the formative pluripotential blast cells that differentiate into the specific types of connective tissues (i.e. the tissues of the body that support the specialized elements; particularly adipose, areolar, osseous, cartilaginous, elastic, marrow stroma, muscle, and fibrous connective tissues) depending upon various in vivo or in vitro environmental influences. Although these cells are normally present at very low frequencies in bone marrow, the inventors of the present invention have discovered a process for isolating, purifying, and greatly replicating the marrow-derived mesenchymal stems cells in culture, i.e. in vitro. This discovery is the subject of U.S. patents and co-pending applications, for example, Caplan and Haynesworth, U.S. Pat. Nos. 5,197,985 and 5,226,914 and PCT Publication No. WO 92/22584 (published 23 Dec. 1992) as well as numerous literature references by Caplan and Haynesworth.

Isolated human hematopoietic stem cells have also been described, for example, in Tsuksamoto et al., U.S. Pat. No. 5,061,620 (October 1991) and reviewed in Edgington, Biotechnology, 10:1099–1106 (1992) and the references cited therein. These are distinguished from MSCs by their ability to differentiate into myeloid and lymphoid blood cells.

In its principal embodiment the invention relates to isolated human mesenchymal stem cells capable of expressing incorporated genetic material of interest. Human stem cells are obtained from the individual donor and rendered substantially isolated from other cells and constituitive donor proteins and other components. It is contemplated that the transformed cells and the expression products of the incorporated genetic material can be used alone or in combination with other cells and/or compositions.

Another aspect of the invention relates to the development of the technology to introduce foreign genes into these progenitor cell cultures, such that all progeny of the cells carry the new genetic material. In addition, cell delivery of the transformed cells is an important component of the process and includes infusion and direct depot injection into periosteal, bone marrow, muscle and subcutaneous sites.

By virtue of the present invention, genes can be introduced into cells which are then returned to the autologous or syngeneic donor where gene expression will effect its therapeutic benefit. Examples of such applications include genes which have a central role in mesenchymal cell maintenance, tissue development, remodeling, repair and in vivo production of extracellular gene products. One example is the gene for normal type I collagen, which can be introduced into the MSCs of osteogenesis imperfecta patients who have a defect in collagen type I.

In addition to the correction of genetic disorders, a unique potential of this technology is the ability to introduce, in a targeted manner, additional copies of essential genes to allow augmented expression of certain gene products. These genes can be, for example, hormones, matrix proteins, cell membrane proteins cytokines, adhesion molecules, detoxification enzymes and "rebuilding" proteins important in tissue repair.

An additional application is the use of introduced genes to alter the phenotype of mesenchymal stem cells and their differentiated progeny for specific therapeutic applications. This includes intracellular gene products, signal transduction molecules, cell surface proteins, extracellular gene expression products and hormone receptors. Disease states and procedures for which such treatments have application include genetic disorders of the musculoskeletal system, diseases of bone and cartilage, the bone marrow, inflammatory conditions, muscle degenerative diseases, malignancies and autologous or allogeneic bone or bone marrow transplantation.

In one embodiment, the isolated human stem cells are preferably mesenchymal stem cells that have been transformed with at least one DNA sequence capable of expressing those translation products capable of packaging a viral sequence so as to be gene therapy producer cells. In a preferred embodiment of this aspect, the isolated human stem cells have been transformed with a DNA sequence comprising a retroviral 5' LTR and, under the transcriptional control thereof, at least one of a retroviral gag, pol or env gene. In another aspect, the isolated human stem cells have also been transformed with a DNA sequence comprising a retroviral packaging signal sequence and incorporated genetic material to be expressed under the control of a promoter therefor so as to be incompetent retroviruses. Also contemplated is the transfection of MSCs or committed stromoblasts to initiate, modulate or augment hematopoiesis.

An additional use of these cells is as gene-transduced producer cells. Defective retrovirus delivery vectors can be inserted into stem cells which thereby become a source of retroviral vectors which, when cocultured in vitro or injected in vivo, deliver genes of interest to targeted areas in an ongoing fashion thereby making it possible to use autologous human cells as producer cells. Thus, the stem cells provide a self-renewing supply of cells carrying the new gene or genes. These cells can be prepared in vitro and introduced one or more times in vivo. Therapy can be initiated by extracting a small number of cells initially and repeated as needed using culture-expanded and even cryopreserved cells. In this way, for example, the patient with osteogenesis imperfecta will slowly and autonomously repopulate skeletal tissue with recombinant type I collagen as the patient's bone grows and remodels.

Virtually all genetic lesions of mesenchymal cells or tissue can be treated or "corrected" by this technology. A key component is the ability to deliver these gene-carrying stem cells to the proper tissue under the conditions that the stem cells will expand and repopulate the tissue space. Patient preparation for introduction of mesenchymal stem cells includes, but is not limited to, (a) marrow ablation by chemotherapy and/or irradiation in conjunction with marrow transplantation, (b) bone or cartilage reconstruction; (c) immunosuppression in the setting of allogeneic cell therapy;

and (d) direct tissue infiltration of "corrected" cells without preparation, particularly where the transduced cells might have a survival advantage, an advantage during differentiation or an advantage in function (such as might be the case when correcting a muscle disorder such as muscular dystrophy with the dystrophin or similar gene). An additional application is in the tagging of MSCs prepared for use in vivo alone or as applied to any indwelling device, such as, for example, an orthopedic device in which it is of interest to "mark" the MSC's and observe their survival, maintenance and differentiation and their association with the device over time.

The advantages provided by the present invention include (a) the ability to culturally expand human stem cells for (re)infusion where they will localize to mesenchymal tissue spaces; (b) the ability to culturally expand and cryopreserve human mesenchymal stem cells which can be used as hosts for stable, heritable gene transfer; (c) the ability to recover genetically altered cells after installation in vivo; (d) the ability to match a genetic therapy to a wide variety of disorders, pinpointing the genetic alteration to the target tissue; and (e) the ability of newly introduced genes within human stem cells and their progeny to be expressed in a less restrictive fashion than other cells, thereby expanding the potential application in treating medical disease.

FIG. 1. Construction of vM5neolacZ: LacZ was cloned into a unique BamHI site of pM5neo. LacZ and neo are transcribed from the MPSV 5' LTR. This is described in detail in Example 1.

Figure 2:
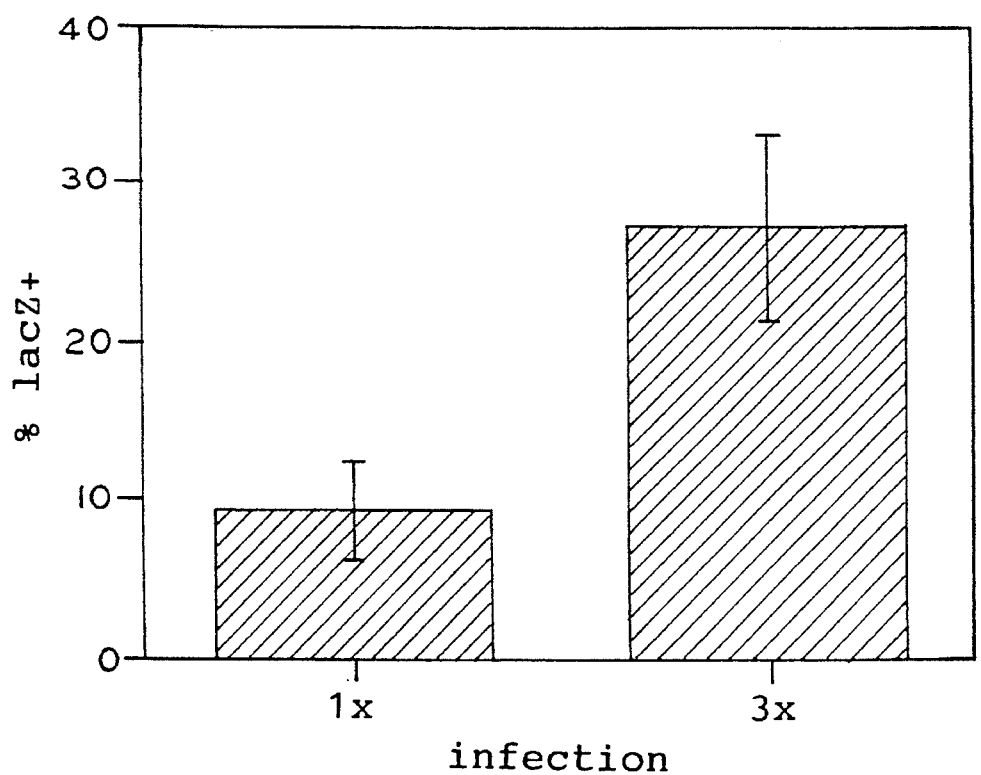

FIG. 2. LacZ expression as a function of retroviral infection: MSCs were infected with vM5neolacZ retroviral supernatant and Polybrene either on one day or three consecutive days. Cells were then plated at low density to allow clusters to form and stained with X-gal. Three daily infections of MSCs increased the efficiency of lacZ expressing colonies 1.5–2.5 fold. This is described in detail in Example 2.

Figure 3:
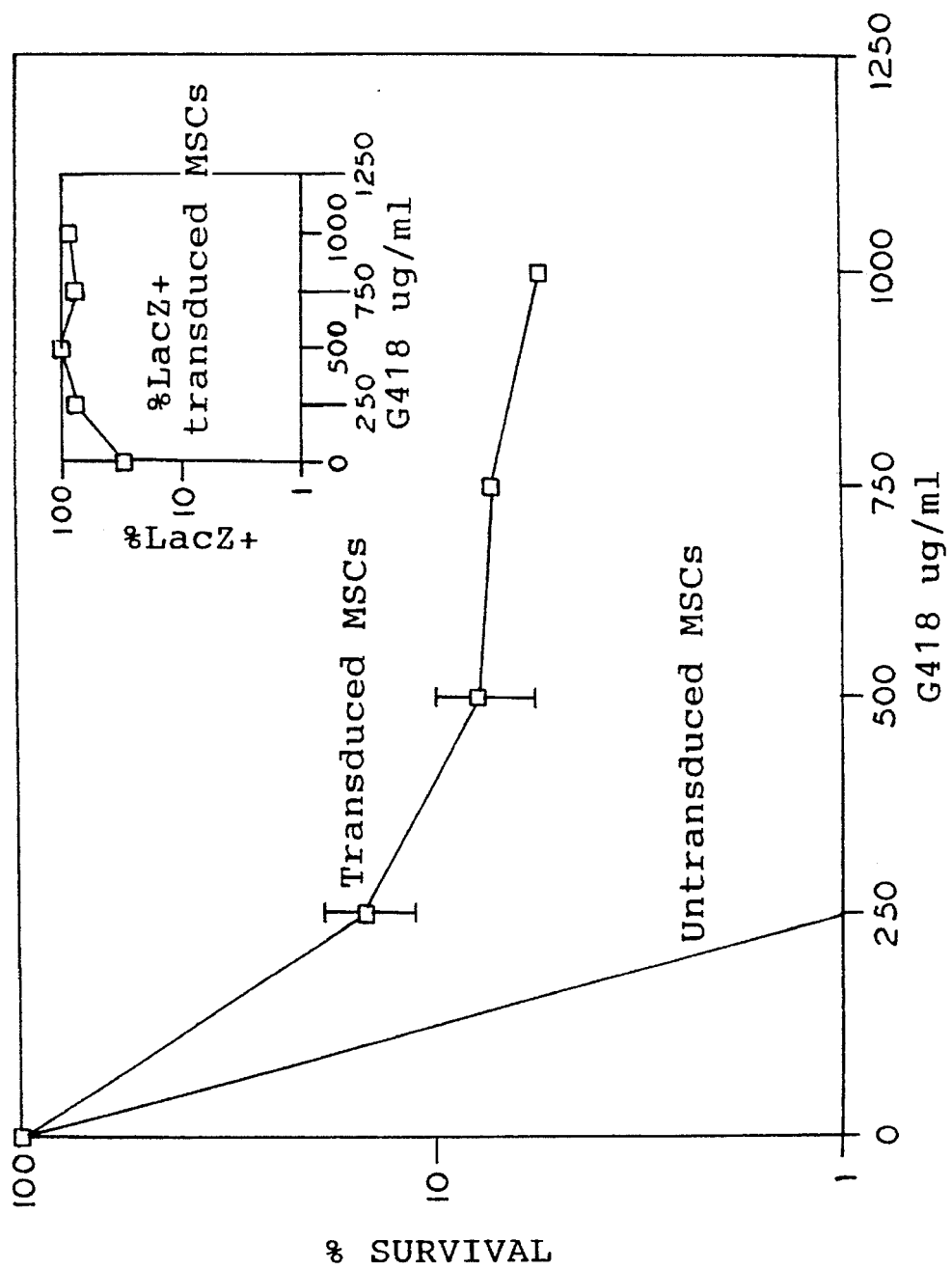
Figure 5A:
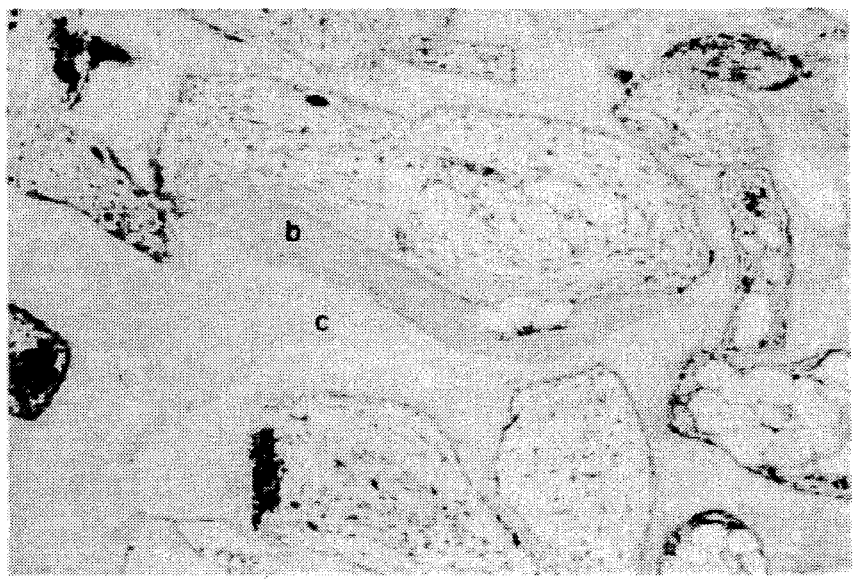
Figure 5B:
Figure 5C:
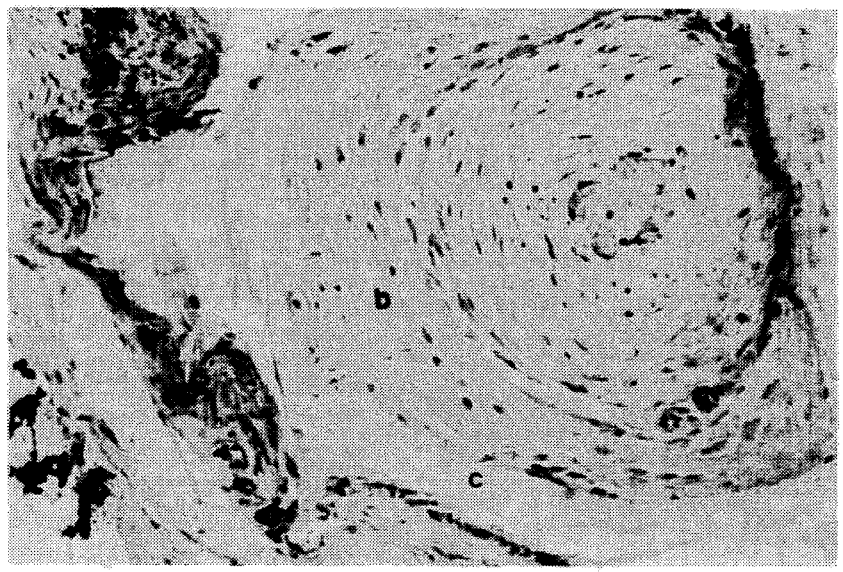
Figure 5D:
Figure 5E:
Figure 5F:
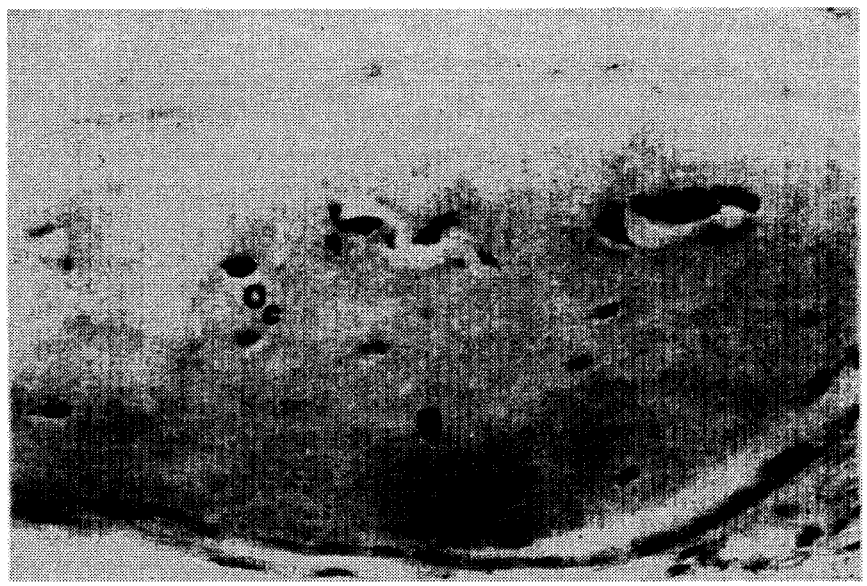
Figure 5G:
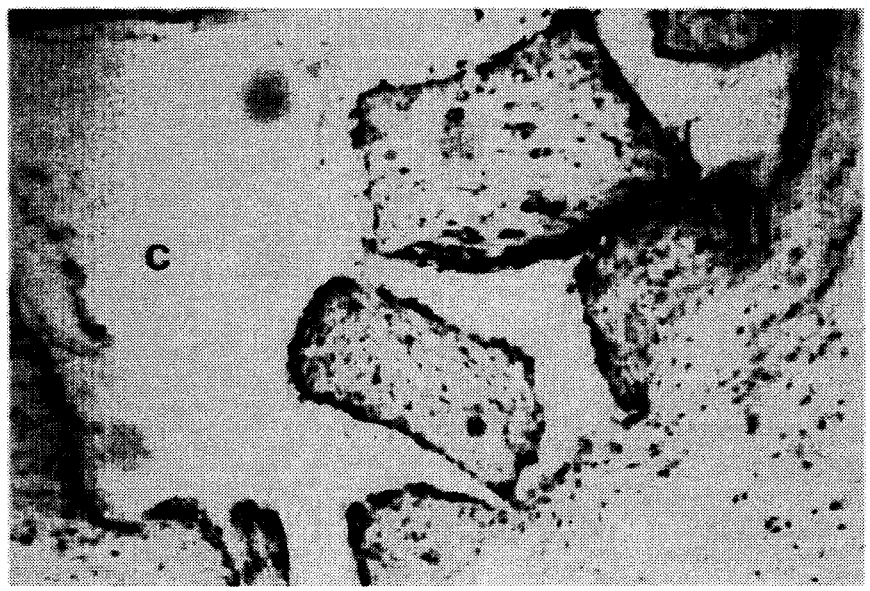

FIG. 3. G418 survival curve and LacZ expression following retroviral transduction: Uninfected MSCs and MSCs retrovirally transduced with vM5neolacZ were plated at $5 \times 10^4$ cells/ml in 12 well plates and selected in 250–1000 µg/ml G418, a neomycin analog (20), for four weeks. Selected colonies were stained with X-gal and counterstained with crystal violet. MSCs infected with vM5neolacZ are G418 resistant and express lacZ at a high frequency. The number of lacZ$^+$ colonies approaches 100% with increased G418 concentration.

FIG. 4. LacZ expression in MSCs In-vitro: MSCs were retrovirally transduced with vM5neolacZ, plated at $5 \times 10^4$ cells/ml with or without G418 for three weeks, stained with X-gal, which stains LacZ$^+$ cells blue, and counterstained with crystal violet which stains the nucleus purple. Colonies shown were selected in G418.

FIGS. 5A–5G. LacZ expression in MSCs and osteocytes following in-vivo growth in ceramic cubes: Untransduced and vMneolacZ transduced MSCs and transduced NIH 3T3 cells were loaded into ceramic cubes and implanted subcutaneously into SCID mice. After six weeks the cubes were removed, fixed and stained for lacZ expression and β-galactosidase product with X-gal. The cubes were then demineralized, embedded in paraffin, sectioned and counterstained with neutral red (A,C,E,F) or Mallory Heidenhain (B,D). The Legend for FIG. 5 is: B bone; C, ceramic; Ob, osteoblast; Oc, osteocyte. The results show that:

A,B) Untransduced MSCs form bone within the ceramics but show no lacZ$^+$ cells.

C–F) Transduced MSCs form bone within the ceramics and lacZ$^+$ (blue) osteocytes within bony lacunae can be seen.

G) Transduced NIH 3T3 cells are lacZ$^+$ within the cube but fail to show bone formation.

The following detailed description, including the definitions that follow below, will aid in a fuller understanding and exemplification of the invention.

As used herein "substantially homologous," which can refer both to nucleic acid and amino acid sequences, means that a particular subject sequence, for example, a mutant sequence, varies from a reference sequence by one or more substitutions, deletions, or additions, the net effect of which does not result in an adverse functional dissimilarity between the reference and subject sequences. For purposes of the present invention, sequences having greater than 90 percent homology, equivalent biological activity, and equivalent expression characteristics are considered substantially homologous. For purposes of determining homology, truncation of the mature sequence should be disregarded. Sequences having lesser degrees of homology, comparable bioactivity, and equivalent expression characteristics are considered equivalents.

As used herein "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, using a cloning vector. Such segments are provided in the form of an open reading frame uninterrupted by internal nontranslated sequences, or introns, which are typically present in eukaryotic genes. Sequences of non-translated DNA may be present downstream from the open reading frame, where the same do not interfere with manipulation or expression of the coding regions.

As used herein "nucleotide sequence" refers to a heteropolymer of deoxyribonucleotides. Generally, DNA segments encoding the proteins provided by this invention are assembled from cDNA fragments and short oligonucleotide linkers, or from a series of oligonucleotides, to provide a synthetic gene which is capable of being expressed in a recombinant transcriptional unit comprising regulatory elements derived from a microbial or viral operon.

As used herein "recombinant expression vector" refers to a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

As used herein "recombinant expression system" means a substantially homogeneous monoculture of human mesenchymal stem cells which have stably integrated a recombinant transcriptional unit into chromosomal DNA or carry the recombinant transcriptional unit as a component of a resident plasmid. In the present case the human mesenchymal stem cells constituting the system are the progeny of a single ancestral transformant. Recombinant expression systems as defined herein will express heterologous protein upon induction of the regulatory elements linked to the DNA segment or synthetic gene to be expressed.

A preferred aspect the invention contemplates the use of human mesenchymal stem cells that include a cell surface epitope specifically bound by antibodies from hybridoma cell line SH2, deposited with the ATCC under accession number HB10743. The human mesenchymal stem cells can further include a cell surface epitope specifically bound by antibodies from hybridoma cell line SH3, deposited with the ATCC under accession number HB10744. The mesenchymal stem cells further include a cell surface epitope specifically bound by antibodies from hybridoma cell line SH4, deposited with the ATCC under accession number HB10745.

In another aspect, the invention contemplates a composition that comprises the transformed mesenchymal stem cells in a medium that stimulates their culture expansion but does not stimulate their differentiation. Preferably the medium comprises a supplemented DMEM particularly wherein the medium includes fetal bovine (e.g. calf) serum. The composition can also be supplemented with an antibiotic and antimycotic composition. In other embodiments of this aspect, the composition comprises the stem cells in supplement $BGJ_b$ medium or supplemented F-12 Nutrient Mixture.

In another aspect of the invention, the stem cells are isolated from other cells by density gradient fractionation, such as by Percoll gradient fractionation. The isolated stem cells are preferably transformed with at least one DNA sequence capable of expressing those translation products capable of packaging a viral sequence.

The structure and life cycle of retroviruses makes them ideally suited to be gene-transfer vehicles since (i) the majority of sequences coding for their structural genes are deleted and replaced by the gene(s) of interest which are transcribed under control of the retroviral regulatory sequences within its long terminal repeat (LTR) region and (ii) they replicate through a DNA intermediate that integrates into the host genome. Although the sites of integration appear to be random with respect to the host genome, the provirus integrates with a defined structure in low copy number. Most of the viral gene sequences can function when supplied in trans. Generally regarding retroviral mediated gene transfer, see McLachlin et al., Progress in Nucleic Acid Research and Molecular Biology, 38:91–135 (1990).

Retroviruses are RNA viruses; that is, the viral genome is RNA. This genomic RNA is, however, reverse transcribed into a DNA intermediate which is integrated very efficiently into the chromosomal DNA of infected cells. This integrated DNA intermediate is referred to as a provirus. As shown in FIG. 1, the retroviral genome and the proviral DNA have three genes: the gag, the pol and the env, which are flanked by two long terminal repeat (LTR) sequences. The gag gene encodes the internal structural (nucleocapsid) proteins, the pol gene encodes the RNA-directed DNA polymerase (reverse transcriptase); and the env gene encodes viral envelope glycoproteins. The 5' and 3' LTRs serve to promote transcription and polyadenylation of virion RNAs.

Adjacent to the 5' LTR are sequences necessary for reverse transcription of the genome (the tRNA primer binding site) and for efficient encapsidation of viral RNA into particles (the Psi site). Mulligan, R. C., In: *Experimental Manipulation of Gene Expression*, M. Inouye (ed). Proceedings of the National Academy of Sciences, U.S.A. 81:6349–6353 (1984).

In order to generate a viral particle containing the recombinant genome, it is necessary to develop cell lines that provide packaging "help". To accomplish this, a plasmid(s), encoding, for example, the retroviral structural genes gag, pol, and env, is introduced into an otherwise untransformed tissue cell line by conventional calcium-phosphate-mediated DNA transfection, Wigler, et al., Cell 11:223 (1977). This plasmid-containing cells are referred to as a "packaging cell line." These plasmid containing packaging cell lines can be maintained as such or a replication incompetent retroviral vector can be introduced into the cell's genome. In the latter case, the genomic RNA generated by the vector construct combines with the constitutively expressed retroviral structural proteins of the packaging line, resulting in the release of retroviral particles into the culture medium. A stable cell line containing the structural gene sequences of the retroviruses is a retroviral "producer cell line."

Because genes can be introduced into progenitor cells using a retroviral vector, they can be "on" (subject to) the retroviral vector control; in such a case, the gene of interest is transcribed from a retroviral promoter. A promoter is a specific nucleotide sequence recognized by RNA polymerase molecules that start RNA synthesis. Alternatively, retroviral vectors having additional promoter elements (in addition to the promoter incorporated in the recombinant retrovirus) which are responsible for the transcription of the genetic material of interest, can be used. For example, a construct in which there is an additional promoter modulated by an external factor or cue can be used, making it possible to control the level of polypeptides being produced by the progenitor cells by activating that external factor of cue. For example, heat shock proteins are proteins encoded by genes in which the promoter is regulated by temperature. The promoter of the gene which encodes the metal-containing protein metallothionine is responsive to cadmium ($Cd^{++}$) ions. Incorporation of this promoter or another promoter influenced by external cues also makes it possible to regulate the production of the polypeptide by the engineered progenitor cells.

It is also possible to use vehicles other than retroviruses to genetically engineer or modify stem cells. Genetic information of interest can be introduced by means of any virus which can express the new genetic material in such cells. For example, SV40, herpes virus, adenovirus and human papilloma virus can be used for this purpose. Many other methods can also be used for introducing cloned eukaryotic DNAs into cultured mammalian cells, several of which are discussed below. The genetic material to be transferred to stem cells may be in the form of viral nucleic acids, bacterial plasmids or episomes. The latter have the advantage of extracellular nephication both in vitro and in vivo.

One of the most widely used methods is transfection mediated by either calcium phosphate or DEAE-dextran. It is believed that the transfected DNA enters the cytoplasm of the cell by endocytosis and is transferred to the nucleus. Up to 20% of a population of cultured cells can be transfected at any one time. Because of its high efficiency, transfection mediated by calcium phosphate or DEAE-dextran is another method of choice for experiments that require expression of the foreign DNA in large numbers of cells. Calcium phosphate-mediated transfection is also used to establish cell lines that carry integrated copies of the foreign DNA, which are usually arranged in head-to-tail tandem arrays.

The polycation Polybrene allows the efficient and stable introduction of low molecular weight DNAs (e.g., plasmid DNAs) into cell lines (e.g., CHO cells) that are relatively resistant to transfection by other methods (Kawai and Nishizawa 1984; Chaney et al. 1986 ).

Protoplasts derived from bacteria carrying high copy numbers of copies of a plasmid of interest can be mixed directly with cultured mammalian cells. After fusion of the cell membranes (usually with polyethylene glycol), the contents of the bacteria are delivered into the cytoplasm of the mammalian cells and the plasmid DNA is transferred to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandemly integrated into the host chromosome (Robert de Saint Vincent et al. 1981). (Schaffner 1980; Rassoulzadegan et al. 1982).

In electroporation the application of brief, high-voltage electric pulses to a variety of cells leads to the formation of nanometer-sized pores in the plasma membrane (Neumann et al. 1982; Zimmermann 1982). DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA (Boggs et al. 1986).

Artificial membrane vesicles (liposomes) are being intensively studied for their usefulness as delivery vehicles in vitro and in vivo. For a review of the current procedures for liposome preparation, targeting, and delivery of contents, see Mannino and Gould-Fogerite (1988). Most of these procedures involve encapsulation of DNA or RNA within liposomes, followed by fusion of the liposomes with the cell membrane. However, Feigner et al. (1987) have reported that DNA that is coated with a synthetic cationic lipid can be introduced into cells by fusion. Although this method is simple and appears to be efficient, it is comparatively new and untested (but see Felgner and Holm 1989; Maurer 1989).

Although direct microinjection into nuclei has the advantage of not exposing DNA to cellular compartments such as low pH endosomes, it cannot be used to introduce DNA on a scale large enough for biochemical analysis. Microinjection is therefore used primarily as a method to establish lines of cells that carry integrated copies of the DNA of interest. (Capecchi 1980).

The present invention makes it possible to genetically engineer mesenchymal human stem cells in such a manner that they produce polypeptides, hormones and proteins not normally produced in human stem cells in biologically significant amounts or produced in small amounts but in situations in which overproduction would lead to a therapeutic benefit. These products would then be secreted into the bloodstream or other areas of the body, such as the central nervous system. The human stem cells formed in this way can serve as a continuous drug delivery systems to replace present regimens, which require periodic administration (by ingestion, injection, depot infusion etc.) of the needed substance.

For example, it can be used to provide continuous delivery of insulin, which at present must be isolated from the pancreas and extensively purified or manufactured in vitro recombinantly and then injected into the body by those whose insulin production or utilization is impaired. In this way, insulin can be introduced into the body via a continuous drug delivery system and, as a result, there would be no need for daily injections of insulin.

Genetically engineered human mesenchymal stem cells can also be used for the production of clotting factors. Hemophiliacs lack a protein called Factor VIII, which is involved in clotting. Factor VIII is now administered by injection. Human stem cells having genes encoding Factor VIII, can be used to make a skin graft (human MSCs are present in the dermis) in which they produce Factor VIII; as a skin graft, the tissue secretes the factor into the bloodstream. Such cells can also be used for continuous delivery of dystrophin to muscle cells fro muscular dystrophy.

Incorporation of genetic material of interest into human stem cells and other types of cells is particularly valuable in the treatment of inherited and acquired disease. In the case of inherited diseases, this approach is used to provide genetically modified human stem cells and other cells which can be used as a metabolic sink. That is, such human stem cells would serve to degrade a potentially toxic substance. For example, this could be used in treating disorders of amino acid catabolism including the hyperphenylalaninemias, due to a defect in phenylalanine hydroxylase; the homocysteinemias, due to a defect in cystathionine β-synthase. Other disorders that could be treated in this way include disorders of amino acid metabolism, such as cystinosis; disorders of membrane transport, such as histidinurea or familial hypecholesterolemia; and disorders of nucleic acid metabolism, such as hereditary orotic aciduria. Human mesenchymal stem cells of the present invention can also be used in the treatment of genetic diseases in which a product (e.g., an enzyme or hormone) normally produced by the body is not produced or is made in insufficient quantities. Here, human stem cells transduced with a gene encoding the missing or inadequately produced substance can be used to produce it in sufficient quantities. This can be used in producing alpha-1 antitrypsin. It can also be used in the production of Factor XIII and Factor IX and thus would be useful in treating hemophilia. For any of these examples, includes in the present invention is the use of tissue specific promoters that allow increased expression in particular mesenchymal cell lineages and cells which would be used to limit gene expression into either the differentiated or precursor stem cell. Examples of such tissue-specific promoters include but are not limited to the promoter for the collagen type I genes or another collagen gene family, the promoter for the dystrophin gene and the promoter for stem cell factor.

There are many acquired diseases for which treatment can be provided through the use of engineered human stem cells (i.e., human stem cells transduced with genetic material of interest). For example, such cells can be used in treating anemia, which is commonly present in chronic disease and often associated with chronic renal failure (e.g., in hemodialysis patients). In this case, human stem cells having incorporated in them a gene encoding erythropoietin would correct the anemia by stimulating the bone marrow to increase erythropoiesis (i.e. production of red blood cells). Other encoded cytokines can be G-CSF or GM-CSF, for example.

Human stem cells of the present invention can also be used to administer a low dose of tissue plasminogen activator as an activator to prevent the formation of thrombi. In this case, human stem cells having incorporated genetic material which encodes TPA would be transplanted into an individual in whom thrombus prevention is desired. This would be useful, for example, as a prophylactic against common disorders such as coronary artery disease, cerebrovascular disease, peripheral vascular occlusive disease, vein (e.g., superficial) thrombosis, such as seen in pulmonary emboli, or deep vein thrombosis. Human stem cells which contain DNA encoding calcitonin can be used in the treatment of Paget's Disease, a progressive, chronic disorder of bone metabolism, in which calcitonin is presently administered subcutaneously.

Another application is a subcutaneous implatation of stem cells alone or adhered to a porous ceramic cube device which will house the stem cells and allow them to differentiate in vivo. Another example would be injection of stem cells into muscle where they will differentiate into muscle cells. An example might be a graft having genetically engineered human stem cells is in birth control. Tests are underway now for using a polypeptide hormone called lutenizing hormone releasing hormone (LHRH) in regulating fertility. Continuous administration of LHRH results in a sterile individual; when administration ceases, the individual is again fertile. Rather than taking LHRH injections or oral medication, one could have a small graft which continuously secretes LHRM to provide the same effect. In the event that the person wanted to regain fertility this transplant could be excised; delivery of the polypeptide hormone would cease.

Human stem cells engineered to produce and secrete interleukins (e.g., IL-1, IL-2, IL-3 or IL-4 through IL-11) can be used in several contexts. For example, the result of some of the therapies now used (e.g., chemotherapy) is induction of neutropenia (the presence of abnormally low numbers of neutrophils in the blood), often caused by direct suppression of the bone marrow. For example, use of virtually all the chemotherapeutic agents, results in neutropenia. This condition results in numerous life-threatening infections. In these cases, administration of, for example, IL-3 through transplantation of human stem cells which contain genetic material encoding IL-3 can be used to increase the neutrophil count. In addition, the administration of thrombopoietin, which stimulates the production of platelets, can be used in the treatment of numerous conditions in which platelet count is low. In this case, human stem cells transduced with the gene for thrombopoietin can be applied to an individual; production and secretion of the encoded product will result in stimulation of platelet production.

Another use of the present invention is in the treatment of enzyme defect diseases. In this case the product (polypeptide) encoded by the gene introduced into human stem cells is not secreted (as are hormones); rather, it is an enzyme which remains inside the cell. There are numerous cases of genetic diseases in which an individual lacks a particular enzyme and is not able to metabolize various amino acids or other metabolites. The correct genes for these enzymes could be introduced into the stem cells and transplanted into the individual; the transplant would then carry out that metabolic function. For example, there is a genetic disease in which those affected lack the enzyme adenosine deaminase. This enzyme is involved in the degradation of purines to uric acid. It is believed possible, using the present invention, to produce a subcutaneous graft as described above capable of producing the missing enzyme at sufficiently high levels to detoxify the blood as it passes through the area to which the graft is applied.

Additional uses not previously possible or suggested include but are not limited to:

1. cytokine genes to enhance hematopoietic reconstitution following marrow transplantation for bone marrow failure for congenital disorders of the marrow
2. bone cytokines to improve repair and healing of injured bone
3. bone matrix problems to improve repair and healing of injured or degenerative bone
4. correction of mesenchymal genetic disorders such as osteogenic imperfecta and muscular dystrophy
5. localized production of proteins, hormones etc. providing cellular therapeutics for many different compounds
6. cytotoxic genes such as thymidine kinase which sensitizes cells to ganciclovir. Gap junction adhesion to tumor cells could allow MSCs to serve for cancer therapy.

The present invention also has veterinary applications. It can be used, for example, in delivering substances such as drugs (e.g., antibiotics) and hormones to animals, which would otherwise be provided by being incorporated into their feed, added to their water or injected periodically (e.g., daily or less frequently). Use of the modified human stem cells of the present invention has the advantage that the tissue formed of the modified cells can be applied to the animal and will provide quantities of the encoded protein on an ongoing basis, thus eliminating the need for daily/periodic administration of the substance.

This invention also has industrial applicability in providing hormones, enzymes and drugs to mammals, including humans, in need of such substances. For example, it can be used to provide a continuous supply of a protein or polypeptide which otherwise would be intermittently administered intravenously, intramuscularly or subcutaneously. It is particularly valuable in providing such substances, such as hormones (e.g., parathyroid hormone, insulin), which are needed in sustained doses for extended periods of time.

Those skilled in the art will recognize, or be able to ascertain using no more than routine experimentation, many equivalents to the specific embodiments of the invention described specifically herein. Such equivalents are intended to be encompassed and exemplified by the following.

EXAMPLE 1

Construction of vM5neolacZ

The vM5neolacZ retroviral vector was constructed in the following manner as described by Clapp et al. (4). Plasmid pM5neo includes the retroviral sequences of the murine Myeloproliferative Sarcoma Virus (MPSV), modified and constructed as described (9) to contain genetic sequences of the 5' and 3' long terminal repeats [LTR] from the MPSV virus (16, 19, 22), denoted in FIG. 1 as "MPSV", splice donor [sd] and splice acceptor [sa] sites from the parent MPSV virus, and the Tn5 neogene from the bacterial transposon 5 which encodes the neomycin resistance gene. When expressed, the neogene confers resistance to the neomycin analogue, G418 (20). These sequences were ligated into the BglII-HindIII site of pBR322 as described (9). The viral region of the plasmid contains a polylinker region of DNA encoding recognition sites for a number of restriction endonucleases of which Bam H1 and Eco R1 are uniquely represented within the viral and plasmid sequence. The U3 region of the MPSV viral 3' LTR contains mutations which allow increased expression within precursor cells such as embryonic stem cells (18, 19, 22) and hematopoietic progenitors (4, 6). The intact sequences for the packaging recognition signal [Psi] required for packaging of these sequences into a retrovirus are 3' to the 5' LTR [see below]. The retroviral sequences contained within the pM5neo plasmid lack the genes essential for retroviral replication and thus is replication defective, as described (McLaughlin et al., supra).

The sequences for the lacZ gene, which encodes the bacterial gene for β-galactosidase, were removed from the pMuMLV-SV-lacZ plasmid (10, 18) after sequential restriction enzyme digestion with Hind III and Bam Hl using standard molecular biology techniques (4,11). This yielded a 3.7 Kb fragment containing the lacZ gene. The 5' and 3' overhanging ends of the lacZ gene fragment were then made blunt by reaction with the Klenow fragment of bacterial DNA polymerase I and then both ends of the fragment were ligated to short sequences of DNA containing recognition sites for the Bam Hl restriction endonuclease [termed Bam Hl linkers] using T4 DNA ligase and standard molecular biology techniques (4,11).

To insert the lacZ gene into the pM5neo retroviral backbone, the plasmid was digested with BamHl restriction endonuclease and treated with phosphatase and the 3.7 Kb DNA fragment consisting of the lacZ gene with Bam Hl linkers at both the 3' and 5' ends was then ligated to pM5neo using DNA ligase by standard molecular biology techniques (4, 11). Following ligation, the plasmid was transformed into DH5alpha cells. Individual transformants were grown, harvested, and analyzed using the method of colony hybridization described by Grunstein (8). Orientation of transformants were confirmed by digestion with Eco Rl restriction endonuclease. The expected 12.3 and 0.4 Kb fragments [see FIG. 1] were observed in multiple colonies. This placed the lacZ gene 5' to the neo gene within the retroviral sequences. mRNA transcripts derived from the LTR of this retrovirus will generate two products: the intact mRNA containing lacZ and neo genes and a spliced mRNA which contains sequences only for the neogene.

Retroviral plasmid pM5neolacZ was isolated and purified from the bacteria by standard techniques (11), and transfected into the GP+envAm-12 [Am-12] retrovirus packaging cell line (12, 13) by Lipofectin Reagent™ according to the instructions of the manufacturer [BRL-GIBCO]. The Am-12 cell line is a helper-free retrovirus producer cell line which was created by transfecting into NIH-3T3 cells, three plasmid DNA sequences. The first one of which contains the retroviral sequences for gag and pol [plasmid pgagpolgpt]. Gag encodes the nucleocapsid protein and pol encodes the retroviral reverse transcriptase both of which are essential for the life cycle of infectious retrovirus as described by McLaughlin, et al. supra). Gpt encodes for a protein which induces resistance to mycophenolic acid and serves as a selectable gene for enrichment of cells carrying the genetic sequences (12, 14). Following electroporation of this plasmid into NIH-3T3 cells, cells were selected for those expressing high levels of the gpt gene in medium containing hypoxanthine (15 μg/ml), xanthine (250 μg/ml) and mycophenolic acid (25 μg/ml) and for high expression of reverse transcriptase (12, 13).

The selected cell clones were co-electroporated with the second and third plasmids: penv-Am, which contains the nucleic acid sequences for the amphotropic envelope protein, env-Am, which, when expressed on the surface of a retrovirus, has a host range of both murine, primate and human cells; and pRSVhyg which contains the nucleic acid sequences for the hyg gene which, when expressed in recipient cells, induces hygromycin resistance (7). Plasmids penv-Am12 and pgagpolgpt contain nucleic acid sequences removed from the 3PO plasmid (14, 15) which includes sequences from the MoMuLV retrovirus beginning at the 5' end of the known sequence including the 5' LTR region encoding the promoter-enhancer region of the MoMuLV which drives expression of the linked genetic sequences [gag, pol, gpt in pgagpolgpt or env in penv-Am] and a deletion of the packaging site region of the MoMuLV.

The advantage of this set of plasmids is that the genes essential for wild-type [normal] function of the MoMuLV are located on two different plasmids and transfected separately into the NIH-3T3 cells. Furthermore, as described above, only after transfection of the replication defective virus are the packaging [Psi] sequences introduced into the cell. Thus, it is unlikely that three different recombinational events will take place between these regions of retroviral sequences in the integrated DNA of the cell to yield sequences which encode an intact infectious retrovirus, and this event has yet to be reported with the Am-12 cell line. As a result, this cell line produces high levels of protein products from the gag, pol and env-Am genes but no infectious retrovirus (12, 13).

Following transfection with pM5neolacZ, the Am-12 cells were grown to confluence in a culture medium which consisted of 50% Dulbecco's Modified Eagle Medium [DMEM] plus 50% F-12 medium supplemented with 7% FCS and 3% calf serum, 1% penicillin-streptomycin solution, 2 mM glutamine and 15 mM HEPES buffer [complete medium]. Heat inactivated (HI) serum [prepared by incubation at 56° C. for 40 minutes] was used to avoid inadvertent inactivation of retrovirus by complement. Thereafter, cultured cells were trypsinized and diluted to allow growth of individual clones while being grown in complete medium in the presence of the neomycin analogue G418 at a concentration of 1 mg/ml. After selection, surviving cells were grown either in the absence of G418 for collection of supernatant containing virus or in 0.2 mg/ml G418 for maintenance of the transduced genes. Supernatant culture medium from confluent cultures was collected, placed at 4° C., passed through a 0.22 micron sterile filter to remove remaining cells but to allow recovery of vM5neolacZ retroviral particles, and stored at −80° C. or used immediately.

Supernatant from these cells was used to infect the ecotropic producer cell line, GP+ E−86. The GP+ E−86 cell line is a helper-free retrovirus producer cell line similar to the Am-12 cell line described above. The GP+E−86 cell line was created by cotransfecting, using electroporation, into NIH-3T3 cells, the plasmid pgagpolgpt [see above] and the plasmid penv which contains the nucleic acid sequences, env, encoding the ecotropic envelope protein (13). Supernatant from the vM5neolacZ-infected GP+E−86 cell line culture was then used to reinfect the AM12 cells originally transfected with pM5neolacZ. In each instance, the infection protocol was identical and cells were selected in G418 at 1 mg/ml.

Clone Am12-lacZ2 (also referred to as "PNL-2") was selected because it gave a high titer of retrovirus quantitated by the ability to transfer G418 resistance and lacZ expression to NIH-3T3 cells using methods previously described (4b). Briefly, supernatant from individual clones of the transduced Am-12 packaging cell line was collected as described above and the concentration of retrovirus quantitated by infecting $2 \times 10^5$ NIH-3T3 cells which had been adhered to 100 mm² dishes 24 hrs previously. The infections were done in a total volume of 1 ml of medium containing limiting dilutions of supernatant [0.01 to 1 μl/plate], 8 μg/ml of Polybrene and 10% heat inactivated fetal calf serum (HI FCS) and dishes were incubated at 37° C. After a six-hour incubation, 10 ml complete medium was added and the growth of the NIH-3T3 cells was allowed to continue until the plates were confluent. Individual clones were analyzed for β-galactosidase activity by staining the retrovirally infected NIH-3T3 cells with 1 mg/ml of X-gal substrate by standard techniques (10). No detectable recombinant wild-type retrovirus was present in the viral supernatant used in these experiments as analyzed by the following experiments. First, NIH-3T3 cells were infected with retroviral supernatant and allowed to grow to confluence. Media from the NIH-3T3 cells was unable to produce G418 resistant colonies when used to infect a second plate of NIH-3T3 cells. Secondly, no provirus was detected in the secondary infections as analyzed by amplification of the neo or lacZ gene. Third, this secondary supernatant could not induce ["rescue"] the release into the supernatant of provirus integrated into NIH-3T3 cells previously infected with the vM5neolacZ virus. Fourth, serum of recipient animals did not contain infectious helper retrovirus when assayed.

Am12-lacZ cells were grown in culture for periods of up to 10 weeks after which early passage cells that had previously been cryopreserved were thawed and used for subsequent passage. Cells were grown in DMEM 50%/F12 50% complete medium, with 7% fetal calf serum and 3% calf serum. To begin virus collection, confluent cells, placed in 100 mm dishes, had removal of culture medium and its replacement by 7 ml of fresh DMEM/F12 with 10% HI FCS. Cells were cultured at 37° C. for 24 hours and medium collected daily for six days. The highest titer of virus was usually collected between days 3 and 6. Retroviral titers of $5-10\times10^5$ CFU/ml [colony forming unit] as defined above. The titer was confirmed for each batch of retroviral supernatant and batches were selected in which the target NIH-3T3 cells which grew in the presence of G418 also expressed the lacZ gene and turned blue following incubation of fixed cells with X-gal. In most instances, cells transduced with the supernatant from Am12-PNL2 cells and selected for G418 resistance were expressing lacZ.

EXAMPLE 2

Description of the Genetic Transduction of MSCs

Human MSCs were cultured from adult bone marrow aspirates as previously described (U.S. Pat. Nos. 5,197,985 and 5,226,914). Normal donors or patients with normal bone marrow undergoing autologous bone marrow harvest in conjunction with treatment for a malignancy (9a). Ten ml bone marrow aspirates were separated by Percoll gradient centrifugation and the mononuclear cells were cultured on plastic tissue culture dishes in DMEM medium with 10% fetal calf serum as previously described (U.S. Pat. No. 5,226,914, (8a)). Similar results were obtained substituting 50% DMEM/50% F-12 medium for DMEM medium. These conditions allow selective attachment of marrow-derived mesenchymal cells which retain the multipotential capacity to differentiate along a number of pathways as previously described (8a,8b). Three days later, nonadherent cells were removed and fresh complete medium was added to the cells.

At first passage, $1-3\times10^5$ cells were placed on plastic tissue culture dishes at a density of approximately 30% confluence in complete medium [DMEM 50%/F12 50% with 30% HI FCS. As noted in Example 1, the HI FCS lacks complement which could inactivate retrovirus upon contact. Four hours after passage, the cells were retrovirally infected as follows: a) medium was removed from the culture dishes; b) 5 ml of viral supernatant from Am-12PNL2 cells [which contains the retrovirus vM5neolacZ as described above at a titer of $5-10\times10^5$ cfu/ml]. The supernatant was prepared as described above, and was added in the presence of 6 µg/ml Polybrene; c) after a 6 hr incubation at 37° C., 5 ml complete medium with 30% HI FCS was added. This procedure was repeated twice on a daily basis. The medium of the culture dishes was changes every 3-4 days and the cells were allowed to grow to 80% confluence, trypsinized to remove them from the plastic dishes as previously described and were split 1:3 into new dishes.

After the third infection with retroviral supernatant, some cultures were exposed to 0.5 mg/ml G418 to select for cells expressing the neogene, using a technique previously described (20), and others were grown to confluence on the dishes. Assessment of cells transduced by this process was made by the level of G418 selection and lacZ expression prior to selection in G418. FIG. 2 shows that 6–30% of the cultured MSCs had evidence of retroviral transduction prior to selection as measured by staining blue after exposure to X-gal) and that three infections was more efficient than one. Cells not carrying the transduced neogene were killed by as little as 0.075 mg/ml G418. Selected cells were allowed to grow to 80% confluence in the presence of 0.5 mg/ml G418 (FIG. 3). Thereafter, they were grown in 0.2 mg/ml G418 with medium change every 3–4 days and were passaged when the cultures became 40–90% confluent by dividing the trypsinized cells 1:3 into new culture dishes. Three to four passages were routinely performed with maintenance of proliferation of the cells and without evidence of differentiation or loss of the mesenchymal phenotype as outlined as 1) to 3) above. At various time points, cells were evaluated for expression of the lacZ gene (FIG. 4) as described below.

Their status as MSCs was confirmed by the following: 1) morphology: cells were fusiform adherent cells with multiple projections without round cell contamination (8a, 8b); 2) surface antigens: cells bound to the SH2, SH3 and SH4 monoclonal antibody which recognize human mesenchymal stem cells using techniques previously described (8b); 3) colony formation in methylcellulose: cells were also noted to have an absence of hematopoietic progenitor cell contamination as indicated by the lack of growth of hematopoietic colonies [colony forming unit-granulocytel/macrophage, CFU-GM; colony forming unit erythroid, CFU-E; burst forming unit-erythrox, PFU-E; or colony forming unit granulocyla, macrophage, erythroid, megakaryocyte, CFU-GEMM] when $1\times10^5$ of these cells were grown in methylcellulose in the presence of recombinant human hematopoietic growth factors including erythropoietin, IL-3, GM-CSF and Stem Cell Factor, using techniques previously described (9a).

Similar experiments were performed with marrow-derived MSCs from rat and mouse. Mononuclear cells flushed from the marrow cavities of Fisher rats and CeH/HeJ mice were cultured for MSCs as previously described (4c) and passaged when 60–80% confluent. Cells were infected with retrovirus as described above for human MSCs except that ecotropic virus derived from the GP$^+$E$^-$86 cell line was used. A similar efficacy of gene transduction and expression of both the neo and lacZ genes was noted in these cells as for human MSCs, ranging from 2–10% of unselected cells. Following selection in 0.5 mg/ml G418, MSC cultures containing uniformly G418 resistant were observed. In these cultures, 50–80% of the cells also expressed the lacZ gene and stained blue after exposure to X-gal reagent (see below). Thus, MSCs from three species have been retrovirally transduced, selected in G418, and culture expanded.

To test the ability of these cells to retain their mesenchymal stem cell phenotype, cells were collected by trypsinization as previously described (8c), centrifuged and resuspended in serum free medium and co-incubated with biphasic ceramic cubes composed of a mixture of tricalcium phosphate and hydroxyapatite (60:40) with a mean pore size of 200 µm. The ceramics were cut into 3×3×3 mm cubes and coated with human fibronectin prior to incubation. After incubation, approximately 5×10⁴ cells adhere to each ceramic cube, as previously described (8a,4c). These coated cubes were then implanted under sterile conditions subcutaneously into the lateral flank of SCID mice, where they were allowed to stay for up to 8 weeks as previously described (4c).

At various time points after culture in vitro and 3, 6 or 8 weeks after being placed in vivo, the cells on plates or cells in cubes were washed twice in PBS and fixed in 1% glutaraldehyde and stained for β-galactosidase with X-gal as previously described (10). Briefly, the cells and cubes were maintained at 22° C. rinsed in 1× PBS and fixed in 2% formaldehyde, 0.2% glutaraldehyde in PBS at 4° C. (cells for 5 mins., cubes for 45 mins.). Both were then rinsed three times in 1× PBS (cubes were incubated in PBS 3 times for 20 mins.). They were stained overnight in 1 mg/ml X-gal, 5 mM potassium ferricyanide, 5 mM potassium ferrocyanide, 2 mM magnesium chloride in PBS at room temperature (Sanes et. al., EMBO 5:3133, 1986). Blue stain within the cytoplasm of cells were detected on the plates by direct visualization and in the cubes after decalcification and section as previously described (4c). Cells on plates and the cell nuclei in the sections were counter-stained with neutral red or crystal violet stain. Cubes were also stained with Mallory-Heidenhain stain to detect the presence of osseous bony material.

The results obtained indicated that between 6–30% of primary human, rat or mouse MSCs in culture could be retrovirally transduced. The gene transfer efficiency was higher in human than mouse or rat due to either optimal growth conditions for the human MSCs or the properties of the amphotropic virus. This efficiency was defined as the percentage of cells staining with X-gal prior to selection in G418, or the proportion of colony forming cells which grew in the presence of 0.5 mg/ml G418 (FIGS. 2 and 3). A high proportion [40–90%] of cells expressing neo and resistant to G-418 also expressed lacZ and stained with X-gal (FIGS. 3 and 4). Presence of the provirus was confirmed by PCR amplification of the neo gene by standard techniques. Retroviral transduction by infection also had no demonstrable effect on cell growth in the absence of selection. Thus, human transduced MSCs could be culture-expanded through 4–7 passages (approximately 20–30 cell divisions) and still maintain their stem cell phenotype. Rodent MSCs, however, grew more slowly and could typically be passaged only 1–2 times before becoming quiescent, and did not expand if passaged more frequently.

When analyzed for the ability to retain their precursor phenotype after selection in G418 and culture expansion, the human MSCs were able to form bone in the ceramic cubes at 6 and 8 wks (FIG. 5). At 3–8 weeks, blue lacZ⁺ cells were detected lining the ceramic cubes and at 6–8 weeks, blue cells embedded within bony lacunae were seen. These results are shown in FIG. 5. The cells lining the calcium phosphate pores of the cube appear to be precursors to osteoblasts whereas those within the lacunae are osteocytes. The pores of the ceramic became filled with host [mouse] connective tissue cells and vasculature, as observed previously (4a, 4c). As a control, NIH-3T3 cells were transduced with retrovirus and selected in G418. These cells were then adhered to the ceramic cubes and placed subcutaneously in the SCID mouse. At 6 weeks, clusters of fibroblastic cells were found within the ceramic pores without evidence of bone formation within the ceramic cubes.

These results indicated: a) that the precursor, genetically transduced MSCs expressed both the neo and lacZ genes when grown under selection pressure of G-418 in vitro; b) that these retrovirally transduced cells retained their "stem cell" phenotype, after in vitro passage for many weeks without evidence of differentiation into osteogenic cells or stromal bone marrow cells, as measured by their ability to differentiate into osteoblasts and osteocytes in vivo, and c) that even when no longer under the selection pressure of G418, these cells retained the ability to express a foreign gene in vivo for at least 8 weeks as they proliferate and pass through the differentiation process, i.e. the genetic transduction has become a stable part of the cellular, genomic DNA. As such, they are unique in being human mesenchymal stem cells derived from a non-fetal, or in this case, adult host which have the capacity to be transduced and culture expanded and have been shown to retain their precursor stem cell phenotype. While loss of the transduced genes occurred in some cells, the majority of cells appear to have retained the proviral genes after a period of prolonged growth in vivo.

EXAMPLE 3

Use of MSCs as Retroviral Producer Cells

Using the plasmid sequences outlined above in example 1, with the present technology, human MSCs can be transduced either by electroporation, lipofection or retroviral gene transfer, with the sequences required to transform these cells into a retroviral producer cell. Thus, human MSCs can be transduced with the plasmids pgagpolgpt, penvAm-12 and pRSVhyg to produce a cell or cell culture which functions much like Am-12. The advantages that the resulting cells have over the current Am-12 cells are the following: a) the cells are not immortalized; b) they can be used as a source of autologous cells for both in vitro and in vivo gene transfer once the replication defective retrovirus carrying the gene of interest is introduced into the cells; c) they can be used as an in vivo source of retrovirus production and thus of gene transfer; and d) they can be used as autologous virus producing cells for studies involving the in vitro or in vivo retroviral transduction of hematopoietic stem cells (which for instance are contained in autologous bone marrow), peripheral hematopoietic progenitors isolated from the blood typically after treatment with a hematopoietic growth factor or chemotherapy or the combination, or are isolated by a variety of procedures from these two sources by the use of physical or monoclonal antibody techniques as described by others. In addition, other selectable genes could be used in the place of the gpt or the hyg gene which potentially offer advantages in the level of cell selection and the ease of use. These include the neogene described above, and other selection genes.

Cited Literature

1.) Akgun E., Ziegler M., Grez M.: Determinants of retrovirus gene expression in embryonal carcinoma cells. J Virol 65:382–388, 1991.
2.) Beck-Engeser G., Stocking C., Just U., Albritton L., Dexter M., Spooncer E., Ostertag W.: Vectors related to the myeloproliferative sarcoma virus allow efficient expression in haematopoietic stem and precursor cell lines, but retroviral infection is reduced in more primitive cells. Hum Gen Ther 2:61–70, 1991.
3.) Bodine D. M., McDonaugh K. T., Brandt S. J., Ney P. A., Agrievla B., Byrne E., Nienhuis A. W.: Development of a high titer retrovirus producing cell line capable of gene transfer into rhesus monkey hematopoietic stem cells. Proc Natl Acad Sci USA 87:3738, 1990.

4a.) Clapp et al, Clapp et al., Fetal liver hematopoietic stem cells as a target for in utero retroviral gene transfer, Blood, 78:1132–1139, 1991

4b.) Davis L. G., Dibner M. D., Battey J. F.: Basic methods in molecular biology, New York: Elsevier, 1986.

4c.) Dennis J. E., Haynesworth S. E., Young R. G. and Caplan A. I. Osteogenesis on marrow-derived mesenchymal cell porous ceramic composites transplanted subcutaneously: effect of fibronectin and laminin on cll etentin and rate of osteogenic expression. Cell Transplantation 1: 23–32, 1992.

5.) Felgner P. L., Gadek T. R., Holm M., Roman R., Chan H. W., Wenz M., Northrop J. P., Ringold G. M., Danielsen M.: New, more efficient method for DNA transfection: Lipofectin™ reagent. Proc Natl Acad Sci USA 84:7413, 1987.

6.) Franz T., Hilberg F., Seliger B., Stocking C., Ostertag W.: Retroviral mutants efficiently expressed in embryonal carcinoma cells. Proc Natl Acad Sci USA 83:3292–3296, 1986.

7.) Gaken J., Farzaneh F., Stocking C., Ostertag W.: Construction of a versatile set of retroviral vectors conferring hygromycin resistance. BioTechniques 13:32–34, 1992.

8a.) Grunstein M., Hogness D. S.: Colony hybridization: A method for isolation of cloned DNAs that contain a specific gene. Proc Natl Acad Sci USA 72:3961–3965, 1975.

8b.) Haynesworth S. E., Goshima J., Goldberg V. M., and Caplan A. I., Characterization of cells with osteogenic potential from human marrow. Bone 13: 81–88, 1992.

8c.) Haynesworth S. E., Baber M. A., and Caplan A. I., Cell surface antigens on human marrow-derived mesenchymal cells are detected by monoclonal antibodies. Bone 13: 69–80, 1992.

9a.) Laker C., Stocking C., Bergholz U., Hess N., DeLamarter J. F., Ostertag W.: Autocrine stimulation after transfer of the granulocyte/macrophage colony-stimulating factor gene and autonomous growth are distinct but interdependent steps in the oncogenic pathway. Proc Natl Acad Sci USA 84:8458–8462, 1987.

9b.) Lazarus H. M. et al., Recombinant granulocyte-macrophage colony-stimulating factor after autologous bone marrow transplantation for relapsed non-Hodgkin's lymphoma. A phase II Eastern Cooperative Oncology Group trial. Blood, 78:830–837, 1991.

10. ) Lin W.-C., Pretlow T. P., Pretlow T. G. II, Culp L. A.: Bacterial lacZ gene as a highly sensitive marker to detect micrometastasis formation during tumor progression. Cancer Res 50:2808–2817, 1990.

11.) Maniatis T., Fritsch E. F., Sambrook J.: Molecular Cloning: A Laboratory Manual. Cold Spring Harboy, New York: Cold Spring Harbor Laboratory, 1982.

12. ) Markowitz D., Goff S., Bank A.: Construction and use of a safe and efficient amphotropic packaging cell line. Virology 167:400–406, 1988.

13.) Markowitz D., Goff S., Bank A.: A safe packaging line for gene transfer: Separating viral genes on two different plasmids. J Virol 62:1120, 1988.

14.) Murphy A. J., Efstratiadis A.: Cloning vectors for expression of cDNA libraries in mammalian cells. Proc Natl Acad Sci USA 84:8277–8281, 1987.

15.) Murphy A. J.: Molecular techniques for the isolation of transcriptional trans-acting factor genes. Doctoral Thesis, Columbia University, 1987.

16a.) Ostertag W., Stocking C., Johnson G. R., Kluge N., Kollek R., Franz T., Hess N.: Transforming genes and target cells of muring spleen-focus-forming viruses. Adv Cancer Res 48: 193–355, 1987.

16b.) Laker et al. Autocrine stimulation after transfer of the granulocyte/macrophage colony-stimulating factor gene and autonomous growth are distinct but interdependent steps in the oncogenic pathway, Proc. Natl. Acad. Sci. USA, 84:8458, 1987.

17.) Podda S., Ward M., Himelstein A., Richardson C., de la Flor-Weiss E., Smith L., Gottesman M., Pastan I., Bank A.: Transfer and expression of the human multiple drug resistance gene into live mice. Proc Natl Acad Sci USA 89:9676–9680, 1992.

18.) Sanes J. R., Rubenstein J. L. R., Nicolas J.-F.: Use of a recombinant retrovirus to study post-implantation cell lineage in mouse embryos. EMBO J, 5:3133–3142, 1986.

19.) Seliger B., Kollek R., Stocking C., Franz T., Ostertag W.: Viral transfer, transcription, and rescue of a selectable myeloproliferative sarcoma virus in embryonal cell lines: Expression of the mos oncogene. Molec & Cell Biol 6:286–293, 1986.

20.) Southern P. J., Berg P.: Transformation of mammalian cells to antibiotic resistance with a bacterial gene under control of the SV40 early region promoter. J Mol Appl Genet, 1:327–341, 1982.

21.) Stocking C., Kollek R., Bergholz U., Ostertag W.: Long terminal repeat sequences impart hematopoietic transformation properties to the myeloproliferative sarcoma virus. Proc Natl Acad Sci USA 82:5746–5750, 1985.

22.) Stocking C., Kollek R., Bergholz U., Ostertag W.: Point mutations in the U3 region of the long terminal repeat of Moloney murine leukemia virus determine disease specificity of the myeloproliferative sarcoma virus. Virology 153:145–149, 1986.

23.) Stocking C., Bergholz U., Friel J., Klinger K., Starke C., Kitamura T., Miyajima A., Ostertag W.: Distinct classes of factor-independent mutants can be isolated after retroviral mutagenesis of a human myeloid stem cell line. Blood (in press).

24.) Valerio D., Einerhand M. P., Wamsley P. M., Bakx T. A., Li C. L., Verma I. M.: Retrovirus-mediated gene transfer into embryonal carcinoma and hemopoietic stem cells: expression from a hybrid long terminal repeat. Gene 84:419–427, 1989.

What is claimed is:

1. Isolated human mesenchymal stem cells which can differentiate into more than one connective tissue type transfected with exogenous genetic material encoding a protein to be expressed.

2. The isolated human mesenchymal stem cells of claim 1 that are non-embryonic mesenchymal stem cells.

3. The isolated human mesenchymal stem cells of claim 1 that are marrow-derived mesenchymal stem cells.

4. The isolated human mesenchymal stem cells of claim 1 that have been transfected with a DNA sequence which codes for at least one protein to be expressed.

5. The isolated human mesenchymal stem cells of claim 4 that have been transfected with a DNA sequence comprising a retroviral 5' LTR and at least one of a retroviral gag, pol or env gene under the transcriptional control of said 5' LTR.

6. The isolated human mesenchymal stem cells of claim 5 that have also been transfected with a DNA sequence comprising a retroviral packaging signal sequence.

7. The isolated human mesenchymal stem cells of claim 1 which include a cell surface epitope specifically bound by antibodies from hybridoma cell line SH2, deposited with the ATCC under accession number HB10743.

8. The isolated human mesenchymal stem cells of claim 7 which further include a cell surface epitope specifically bound by antibodies from hybridoma cell line SH3, deposited with the ATCC under accession number HB10744.

9. The isolated human mesenchymal stem cells of claim 7 which include a cell surface epitope specifically bound by antibodies from hybridoma cell line SH4, deposited with the ATCC under accession number HB10745.

10. A composition comprising the isolated human mesenchymal stem cells of claim 1 in a medium that stimulates their culture expansion but does not stimulate their differentiation.

11. The composition of claim 10 wherein the medium comprises a supplemented DMEM.

12. A composition of claim 11 wherein the medium comprises serum.

13. The composition of claim 12 wherein the medium comprises fetal animal serum.

14. The composition of claim 11 which is supplemented with an antibiotic and antimycotic composition.

15. A composition comprising the isolated human mesenchymal stem cells of claim 1 in supplemented $BGJ_b$ medium.

16. A composition comprising the isolated human mesenchymal stem cells of claim 1 in supplemented F-12 Nutrient Mixture.

17. The composition of claim 1 wherein the isolated human mesenchymal stem cells of claim 1 are isolated from other cells by selective binding with antibodies from hybridoma cell line SH2, deposited with the ATCC under accession number HB10743.

18. The composition of claim 10 wherein the mesenchymal stem cells are isolated from other cells by density gradient fractionation.

19. The composition of claim 10 wherein the mesenchymal stem cells are isolated from other cells by Percoll gradient fractionation.

20. The isolated human mesenchymal stem cells of claim 4 that have been transduced with a retroviral vector that includes the DNA sequence that codes for the protein to be expressed.

21. The isolated human mesenchymal stem cells of claim 20 wherein transcription of the DNA sequence is under the control of a retroviral LTR.

\* \* \* \* \*